US012616411B2

(12) United States Patent
Engebretsen et al.

(10) Patent No.: US 12,616,411 B2
(45) Date of Patent: May 5, 2026

(54) OVERRIDING LONGEST RR INTERVALS

(71) Applicant: Preventice Solutions, Inc., Rochester, MN (US)

(72) Inventors: David Robert Engebretsen, Cannon Falls, MN (US); Timothy Patrick McClanahan, Rochester, MN (US); Michael Thomas Edward McRoberts, Mazeppa, MN (US); Jan Hagenbrock, Rochester, MN (US); David Robert Will, Rochester, MN (US)

(73) Assignee: Preventice Solutions, Inc., Rochester, MN (US)

( * ) Notice: Subject to any disclaimer, the term of this patent is extended or adjusted under 35 U.S.C. 154(b) by 308 days.

(21) Appl. No.: 18/139,686

(22) Filed: Apr. 26, 2023

(65) Prior Publication Data

US 2023/0346290 A1     Nov. 2, 2023

Related U.S. Application Data

(60) Provisional application No. 63/335,629, filed on Apr. 27, 2022.

(51) Int. Cl.
*A61B 5/352*     (2021.01)
*A61B 5/00*     (2006.01)

(52) U.S. Cl.
CPC .............. *A61B 5/352* (2021.01); *A61B 5/743* (2013.01); *A61B 5/7475* (2013.01)

(58) Field of Classification Search
CPC ....... A61B 5/0006; A61B 5/346; A61B 5/352; A61B 5/364; A61B 5/7264; A61B 5/743; A61B 5/7475; G06N 3/0464; G06N 3/048; G16H 15/00; G16H 40/63; G16H 40/67; G16H 50/20; G16H 50/70
See application file for complete search history.

(56) References Cited

U.S. PATENT DOCUMENTS

2022/0071535 A1*   3/2022   Jernigan   .............. A61B 5/0205

* cited by examiner

*Primary Examiner* — George Manuel
(74) *Attorney, Agent, or Firm* — Faegre Drinker Biddle & Reath LLP

(57)     ABSTRACT

A method includes receiving a package of data comprising electrocardiogram (ECG) data and metadata. The metadata includes determined RR intervals associated with the ECG data. The method further includes displaying, on a user interface, at least a subset of the determined RR intervals and overriding the determined RR intervals associated with a time period that is greater than a time period associated with a selected RR interval.

15 Claims, 9 Drawing Sheets

302 Receive ECG data and metadata associated with the ECG data, including RR intervals 304 Display, on a user interface, at least a subset of determined RR intervals 306 Override the determined RR intervals associated with a time period that is greater than a time period associated with a selected RR interval

300

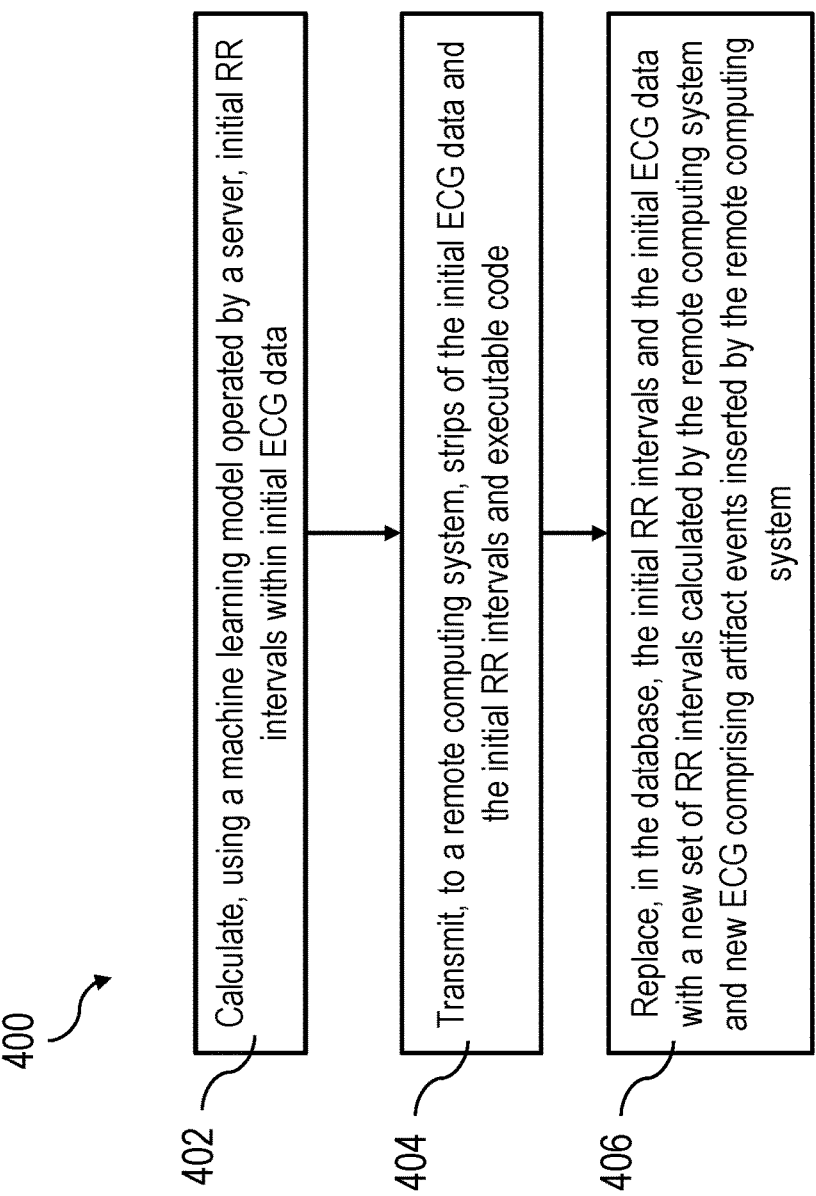

400

402 Calculate, using a machine learning model operated by a server, initial RR intervals within initial ECG data 404 Transmit, to a remote computing system, strips of the initial ECG data and the initial RR intervals and executable code 406 Replace, in the database, the initial RR intervals and the initial ECG data with a new set of RR intervals calculated by the remote computing system and new ECG comprising artifact events inserted by the remote computing system

FIG. 8

OVERRIDING LONGEST RR INTERVALS

CROSS REFERENCE TO RELATED APPLICATION

This application claims priority to Provisional Application No. 63/335,629, filed Apr. 27, 2022, all of which are herein incorporated by reference in their entirety.

TECHNICAL FIELD

The present disclosure relates to devices, methods, and systems for analyzing cardiac activity and cardiac events.

BACKGROUND

Monitoring devices for collecting biometric data are becoming increasingly common in diagnosing and treating medical conditions in patients. For example, mobile devices can be used to monitor cardiac data in a patient. This cardiac monitoring can empower physicians with valuable information regarding the occurrence and regularity of a variety of heart conditions and irregularities in patients. Cardiac monitoring can be used, for example, to identify abnormal cardiac rhythms, so that critical alerts can be provided to patients, physicians, or other care providers and patients can be treated.

SUMMARY

In Example 1, a method includes receiving a package of data that includes electrocardiogram (ECG) data and metadata. The metadata includes determined RR intervals associated with the ECG data. The method further includes displaying, on a user interface, at least a subset of the determined RR intervals and overriding the determined RR intervals associated with a time period that is greater than a time period associated with a selected RR interval.

In Example 2, the method of Example 1, wherein the overriding the determined RR intervals is performed in response to receiving, via the user interface, a user selection of the selected RR interval.

In Example 3, the method of any of the preceding Examples, wherein the selected RR interval is a longest true RR interval of the subset of the determined RR intervals.

In Example 4, the method of any of the preceding Examples, further comprising calculating a time period for a longest determined RR interval based on the selected RR interval.

In Example 5, the method of any of the preceding Examples, wherein each of the subsets of determined RR intervals includes ECG data over multiple beats.

In Example 6, the method of any of the preceding Examples, wherein each of the overridden determined RR intervals is associated with ECG data comprising an unclassified beat.

In Example 7, the method of any of the preceding Examples, wherein each of the overridden determined RR intervals is associated with an incorrect RR interval time period.

In Example 8, the method of any of the preceding Examples, wherein the overriding includes inserting an artifact event between respective pairs of beats.

In Example 9, the method of claim 8, wherein the artifact event is inserted at a predetermined period of time before the later-occurring of the respective pairs of beats.

In Example 10, the method of any of the preceding Examples, further comprising recalculating RR interval data after the overriding the determined RR intervals.

In Example 11, the method of any of the preceding Examples, wherein each RR interval is associated with a pair of beats.

In Example 12, the method of any of the preceding Examples, wherein each RR interval is a length of time between a pair of R-waves within the ECG data.

In Example 13, a computer program product comprising instructions to cause one or more processors to carry out the steps of the method of Examples 1-12.

In Example 14, a computer-readable medium having stored thereon the computer program product of Example 13.

In Example 15, a computer comprising the computer-readable medium of Example 14.

In Example 16, a system includes a remote computing system with: a user interface (UI), a first processor, and a first computer-readable medium having a first set of computer-executable instructions embodied thereon. The first set of instructions are configured to be executed by the first processor to cause the first processor to perform various steps. One step includes—after receiving a package of data comprising ECG data and metadata including determined RR intervals associated with the ECG data—display, on the UI, at least a subset of the determined RR intervals. Another step includes override the determined RR intervals associated with a time period that is greater than a time period associated with a selected RR interval.

In Example 17, the system of Example 16, wherein the selected RR interval is a user-selected RR interval.

In Example 18, the system of Example 16, wherein the selected RR interval is a longest true RR interval of the subset of the determined RR intervals.

In Example 19, the system of Example 16, wherein each of the RR intervals in the subset of determined RR intervals includes ECG data over multiple beats.

In Example 20, the system of Example 16, wherein each of the overridden determined RR intervals is associated with ECG data comprising an unclassified beat.

In Example 21, the system of Example 16, wherein each of the overridden determined RR intervals is associated with an incorrect RR interval time period.

In Example 22, the system of Example 16, wherein the first set of instructions are configured to be executed by the first processor to cause the first processor to: insert an artifact event between respective pairs of beats in each of the overridden RR intervals.

In Example 23, the system of Example 22, wherein the artifact events are inserted at predetermined periods of time before the later-occurring of the respective pairs of beats.

In Example 24, the system of Example 16, wherein the first set of instructions are part of the package of data received from a server.

In Example 25, the system of Example 24, wherein the first set of instructions are executed by a web browser at the remote computing system.

In Example 26, the system of Example 16, further including a server with: a database, a second processor, and a second computer-readable medium having a second set of computer-executable instructions embodied thereon. The second set of instructions are configured to be executed by the second processor to cause the second processor to carry out various steps. The steps include: calculate, using a machine learning model operated by the server, the determined RR intervals; store the determined RR intervals in the database; transmit, to the remote computing system, strips of the ECG data and the determined RR intervals and the first set of instructions; receive a modified set of RR intervals; and replace, in the database, the determined RR intervals with the modified set of RR intervals.

In Example 27, a method includes receiving a package of data comprising ECG data and metadata. The metadata includes determined RR intervals associated with the ECG data. The method further includes displaying, on a user interface, at least a subset of the determined RR intervals and overriding the determined RR intervals associated with a time period that is greater than a time period associated with a selected RR interval.

In Example 28, the method of Example 27, wherein the overriding the determined RR intervals is performed in response to: receiving, via the user interface, a user selection of the selected RR interval.

In Example 29, the method of Example 27, wherein each of the overridden determined RR intervals is associated with ECG data comprising an unclassified beat.

In Example 30, the method of Example 27, wherein the overriding includes inserting an artifact event between respective pairs of beats.

In Example 31, the method of Example 30, wherein the artifact event is inserted at a predetermined period of time before the later-occurring of the respective pairs of beats.

In Example 32, the method of Example 27, further comprising recalculating RR interval data after the overriding the determined RR intervals.

In Example 33, the method of Example 27, wherein each RR interval is a length of time between a pair of R-waves within the ECG data.

In Example 34, a method includes calculating, using a machine learning model operated by a server, initial RR intervals within initial ECG data; storing the initial RR intervals in a database of the server; transmitting, to a remote computing system, strips of the initial ECG data and the initial RR intervals and executable code; receiving a modified set of RR intervals at the server, wherein the modified set of RR intervals include overridden RR intervals having a time period that is greater than a time period associated with a selected longest RR interval; and replacing, in the database, the initial RR intervals with the modified set of RR intervals.

In Example 35, the method of Example 34, further comprising training the machine learning model with the modified set of RR intervals.

While multiple instances are disclosed, still other instances of the present disclosure will become apparent to those skilled in the art from the following detailed description, which shows and describes illustrative instances of the disclosure. Accordingly, the drawings and detailed description are to be regarded as illustrative in nature and not restrictive.

BRIEF DESCRIPTION OF THE DRAWINGS

FIG. 8 shows a flow diagram depicting an illustrative method for hosting a SaaS platform and for overriding RR intervals, in accordance with instances of the disclosure.

Figure 1:
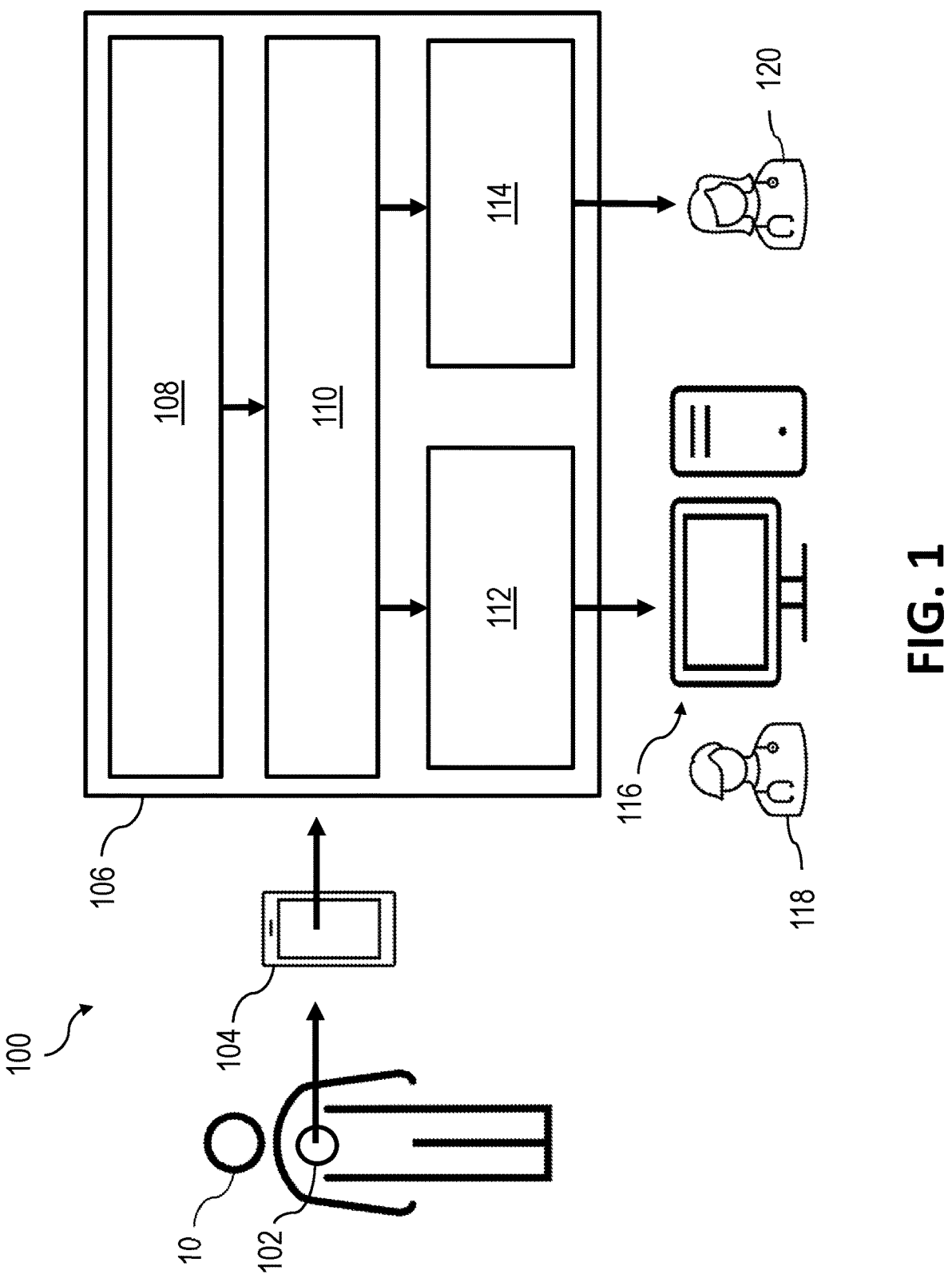
FIG. 1 shows a cardiac monitoring system, in accordance with certain instances of the present disclosure.

While the disclosed subject matter is amenable to various modifications and alternative forms, specific instances have been shown by way of example in the drawings and are described in detail below. The intention, however, is not to limit the disclosure to the particular instances described. On the contrary, the disclosure is intended to cover all modifications, equivalents, and alternatives falling within the scope of the disclosure as defined by the appended claims.

DETAILED DESCRIPTION

The present disclosure relates to devices, methods, and systems for facilitating analysis of cardiac activity and cardiac events (e.g., abnormal cardiac rhythms or other issues).

Electrocardiogram (ECG) data of a patient can be used to monitor cardiac activity and/or identify whether the patient has experienced a cardiac event. One type of cardiac activity measurement is referred to as an RR interval. RR intervals represent the time elapsed between two successive R-waves of QRS portions of ECG data. Put another way, RR intervals measure the time between two peaks of successive R-waves. When reviewing a patient's cardiac activity, a physician may want to know what the length of the longest RR interval during a study was. However, determining the longest RR interval (or sets of longest RR intervals) can be challenging because of noise in ECG data and/or unidentified R-waves. Certain instances of the present disclosure are accordingly directed to systems, methods, and devices for assisting with determining RR intervals.

FIG. 1 illustrates a patient 10 and an example system 100. The system 100 includes a monitor 102 attached to the patient 10 to detect cardiac activity of the patient 10. The monitor 102 may produce electric signals that represent the cardiac activity in the patient 10. For example, the monitor 102 may detect the patient's heart beating (e.g., using infrared sensors, electrodes) and convert the detected heartbeat into electric signals representing ECG data. The monitor 102 communicates the ECG data to a mobile device 104 (e.g., a mobile phone).

The mobile device 104 may include a program (e.g., mobile phone application) that receives, processes, and analyzes the ECG data. For example, the program may analyze the ECG data and detect or flag cardiac events (e.g., periods of irregular cardiac activity) contained within the ECG data. Because ECG data may be getting continuously generated, the amount of ECG data can be overwhelming to store and process locally on the mobile device 104. As such, the mobile device 104 can periodically transmit chunks of the ECG data to another device or system, which can process, append together, and archive the chunks of the ECG data and metadata (e.g., time, duration, detected/flagged cardiac events) associated with the chunks of ECG data. In certain instances, the monitor 102 may be programmed to transmit the ECG data directly to the other device or system without utilizing the mobile device 104. Also, in certain instances, the monitor 102 and/or the mobile device 104 includes a button or touch-screen icon that allows the patient 10 to initiate an event. Such an indication can be recorded and communicated to the other device or system. In other instances involving multi-day studies, the ECG data and associated metadata are transmitted in larger chunks.

Cardiac Event Server

In the example shown in FIG. 1, the mobile device 104 transmits the ECG data (and associated metadata, if any) to a cardiac event server 106 (hereinafter "the server 106" for brevity). The server 106 includes multiple platforms, layers, or modules that work together to process and analyze the ECG data such that cardiac events can be detected, filtered, prioritized, and ultimately reported to a patient's physician for analysis and treatment. In the example of FIG. 1, the server 106 includes one or more machine learning models 108 (e.g., deep neural networks), a cardiac event router 110, a report platform 112, and a notification platform 114. Although only one server 106 is shown in FIG. 1, the server 106 can include multiple separate physical servers, and the various platforms/modules/layers can be distributed among the multiple servers. Each of the platforms/modules/layers can represent separate programs, applications, and/or blocks of code where the output of one of the platforms/modules/layers is an input to another of the platforms/modules/layers. Each platform/module/layer can use application programming interfaces (APIs) to communicate between or among the other platforms/modules/layers as well as systems and devices external to the server 106.

The server 106 applies the machine learning model 108 to the ECG data to determine various cardiac data and events. As one example, the machine learning model 108 may determine the RR intervals of the beats within the ECG data. However, because of noise in the ECG data, the machine learning model 108 may not recognize each beat. When a beat is not recognized, the determined RR interval will be longer than the true RR interval between successive beats.

In certain embodiments, the machine learning model 108 includes two paths, where the first path is a deep convolutional neural network and the second path is a deep fully-connected neural network. The deep convolutional neural network receives one or more sets of beats (e.g., beat trains with 3-10 beats) which are processed through a series of layers in the deep convolutional neural network. The series of layers can include a convolution layer to perform convolution on time series data in the beat trains, a batch normalization layer to normalize the output from the convolution layer (e.g., centering the results around an origin), and a non-linear activation function layer to receive the normalized values from the batch normalization layer. The beat trains then pass through a repeating set of layers such as another convolution layer, a batch normalization layer, a non-linear activation function layer. This set of layers can be repeated multiple times.

The deep fully connected neural network receives RR-interval data (e.g., time intervals between adjacent beats) and processes the RR-interval data through a series of layers: a fully connected layer, a non-linear activation function layer, another fully connected layer, another non-linear activation function layer, and a regularization layer. The output from the two paths is then provided to the fully connected layer. The resulting values are passed through a fully connected layer and a softmax layer to produce probability distributions for the classes of beats.

If the machine learning model 108 determines that the ECG data most closely resembles a labeled ECG data associated with a cardiac event, then the machine learning model 108 may determine that the patient 10 has experienced that cardiac event. Additionally, the machine learning model 108 may measure or determine certain characteristics of the cardiac activity of the patient 10 based on the ECG data. For example, the machine learning model 108 may determine a heart rate, a duration, or a beat count of the patient 10 during the cardiac event based on the ECG data. The machine learning model 108 may also determine a confidence level for each classification or identification of a cardiac event. The confidence level is an indication of certainty or uncertainty in the accuracy of the machine learning model's classification or identification. The server 106 stores the cardiac event (and associated metadata such as information like heart rate, duration, beat count, etc.) in a database for storage. Subsequently, the server 106 may retrieve the cardiac event and associated information from the database.

In certain instances, the mobile device 104 (or monitor 102) may initially classify a cardiac event based on the ECG data. The server 106 may then re-classify or confirm the cardiac event using the machine learning model 108. Doing so allows for a more computationally-expensive analysis of the ECG data to be performed using the computing resources of the server 106, rather than the limited resources of the mobile device 104.

In certain instances, once the ECG data is processed by the machine learning model 108, the ECG data is made available for the report platform 112. As will be described in more detail below, the report platform 112 can be accessed by a remote computer 116 (e.g., client device such as a laptop, mobile phone, desktop computer, and the like) by a user at a clinic or lab 118.

In other instances, the cardiac event router 110 is used to determine what platform further processes the ECG data based on the classification associated with the cardiac event. For example, if the identified cardiac event is severe, the cardiac event router 110 can flag or send the ECG data, etc., to the notification platform 114. The notification platform 114 can be programmed to send notifications (along with relevant ECG data and associated metadata) immediately to the patient's physician/care group remote computer 116 and/or to the patient 10 (e.g., to their computer system, e-mail, mobile phone application).

Figure 2:
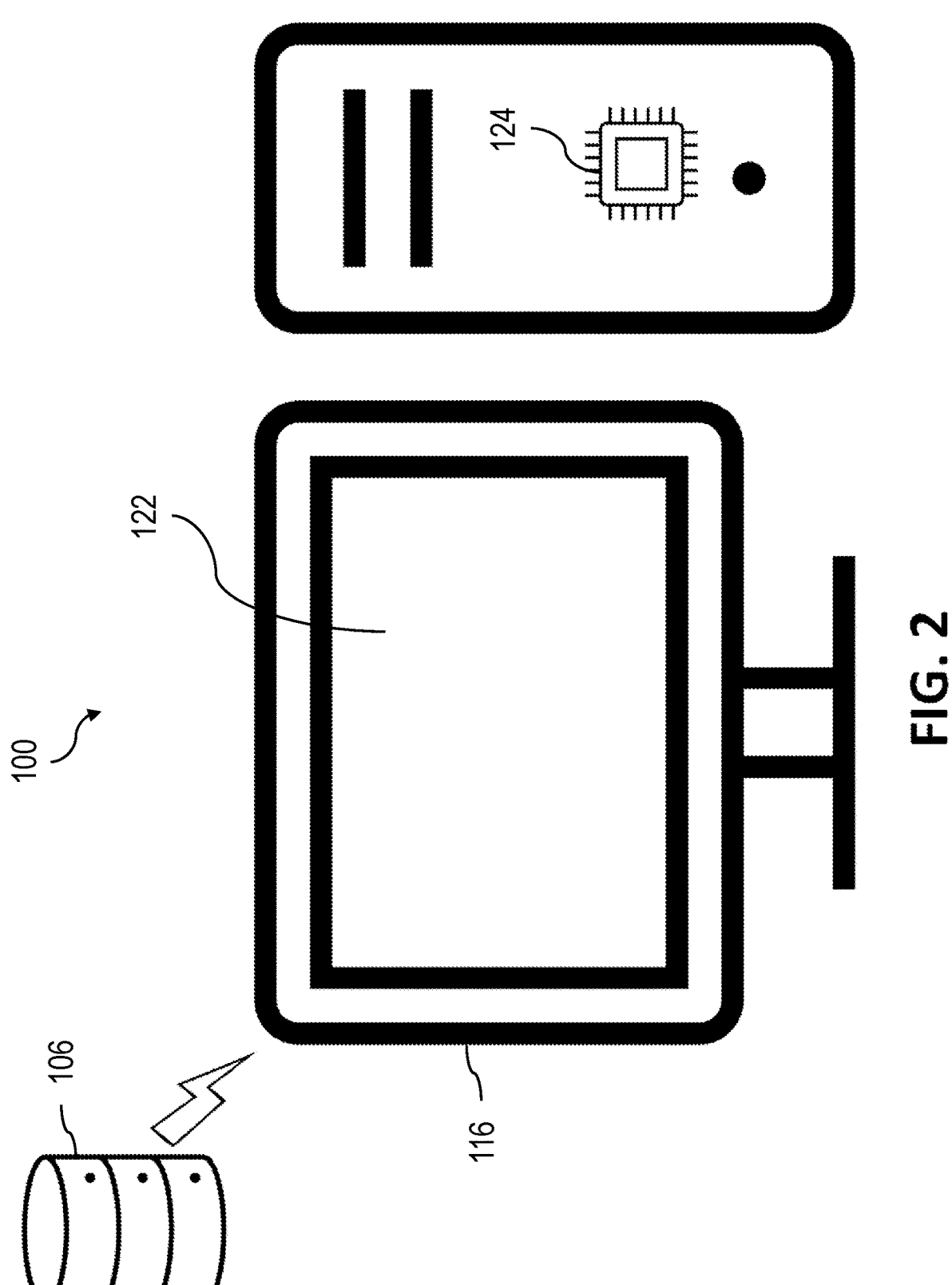
FIG. 2 shows a server, remote computer, and user interface, in accordance with certain instances of the present disclosure.

FIG. 2 shows the server 106 communicatively coupled (e.g., via a network) to the remote computer 116. In the example of FIG. 2, the remote computer 116 includes a monitor showing a user interface 122 (hereinafter "the UI 122" for brevity) that displays features of the report platform 112 hosted by the server 106. The UI 122 includes multiple pages or screens for tracking and facilitating analysis of patient ECG data.

In certain instances, the report platform 112 is a software-as-a-service (SaaS) platform hosted by the server 106. To access the report platform 112, a user (e.g., a technician) interacts with the UI 122 to log into the report platform 112 via a web browser such that the user can use and interact with the report platform 112. When the user at the clinic or lab 118 is ready to analyze ECG data of a patient, the user can select a patient's profile through the UI 122.

The server 106 (e.g., via programming associated with the report platform 112) can start a process for sending data to the remote computer 116. This data includes the ECG data and metadata associated with the ECG data. As noted above, once the ECG data from the monitored patients has been collected, the machine learning model 108 may determine certain characteristics of the cardiac activity of the patient 10 based on the ECG data, including estimating that a cardiac event has occurred and associating or generating metadata for the determined events. The metadata can include information about the patient 10, a heart rate of the patient 10 during the cardiac event, a duration of the cardiac event, a beat count of the cardiac event, a confidence level of the machine learning model's identification of the cardiac event, and/or a beat classification (e.g., normal, ventricular, supraventricular, unclassified). In certain embodiments, the machine learning model 108 assigns each beat with a beat classification and also assigns, for certain groups and patterns of beats, a cardiac event type (e.g., atrial fibrillation, ventricular tachycardia, flutter). To distinguish among the beats, each individual beat can therefore be assigned a unique identifier (e.g., a unique number).

Accessing, processing, and displaying one or more days' worth of ECG data and metadata can consume a large amount of computing resources, network bandwidth resources, and human resources. To help alleviate burdens on these resources, the server 106 (e.g., via the report platform 112) can selectively transmit packages of ECG data and metadata to the remote computer 116.

The initial packages of data can include: (1) short strips (e.g., 60-second strips) of ECG data surrounding detected cardiac events, (2) metadata associated with the strips, and (3) executable code (e.g., JavaScript code). In certain instances, only the ECG data associated with highest priority cardiac events are initially transferred. After the initial packages of data are transmitted from the server to the remote computer 116, additional packages of data can be transmitted in response to selections made by the user in the UI 1122.

Report Page

Figure 3:
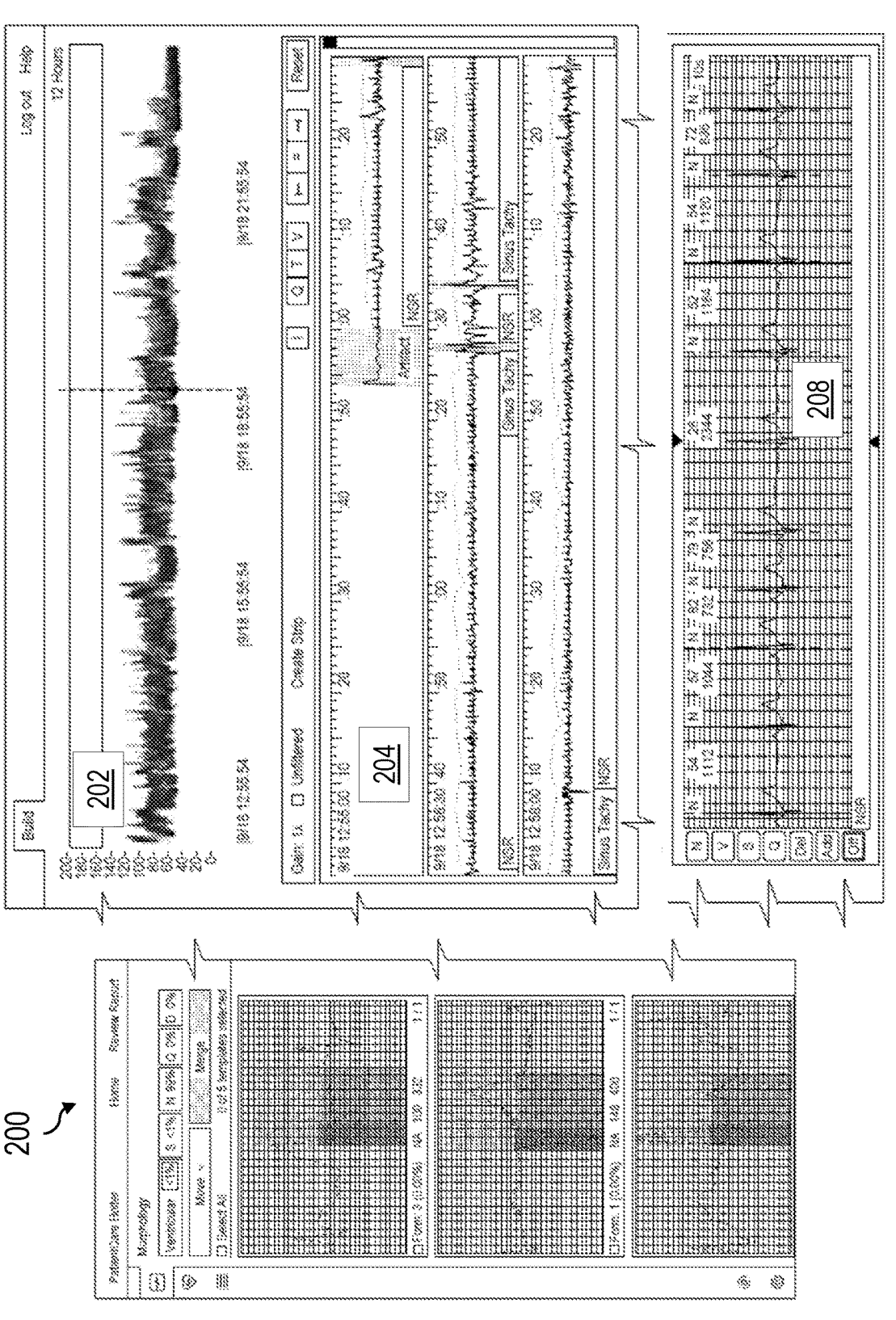
FIG. 3 shows a view of a report building page, in accordance with certain instances of the present disclosure.
Figure 4:
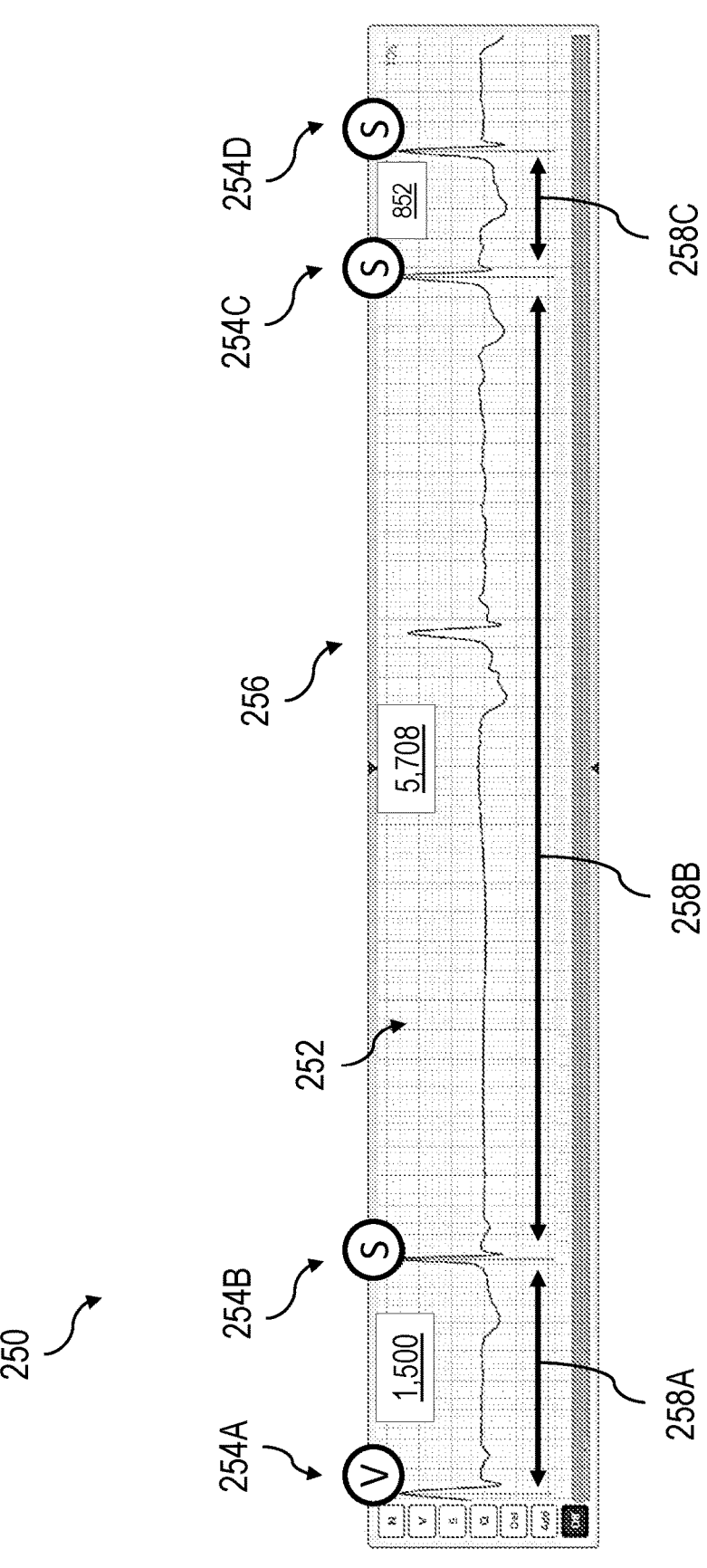
FIGS. 4-6 show different views or sections of an RR interval summary page, in accordance with certain instances of the present disclosure.
Figure 5:
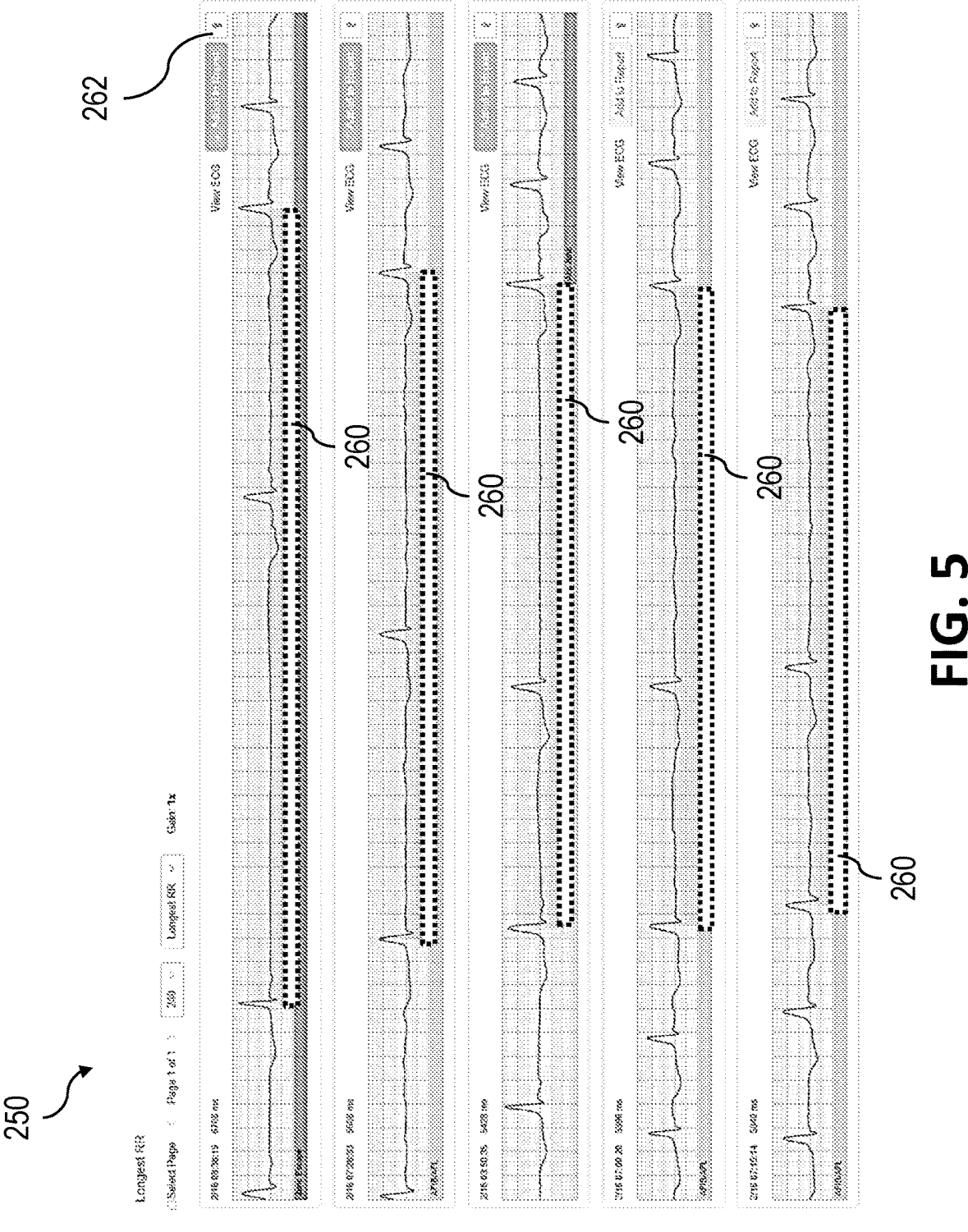
Figure 6:
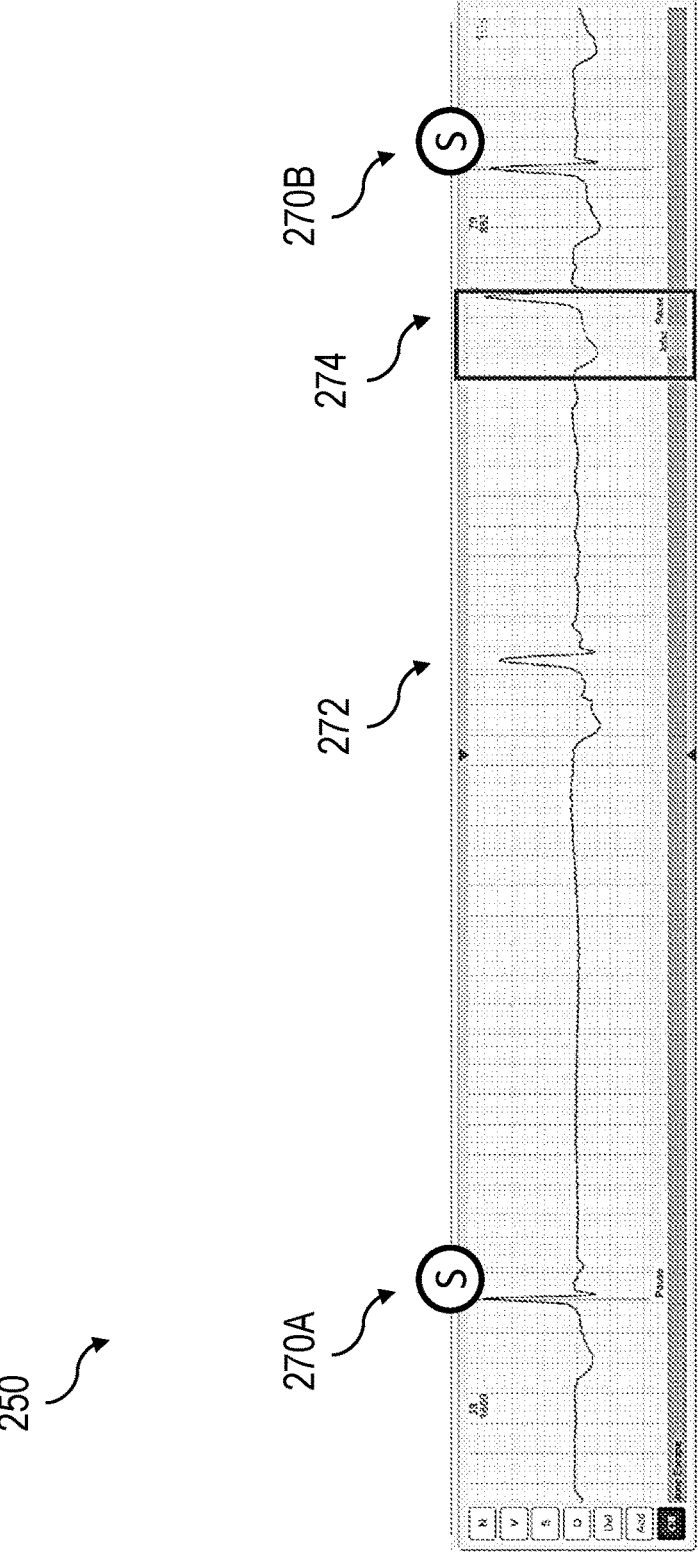

With the initial packages of data received at the remote computer 116, the user has access (via the UI 122) to a report build page 200 shown in FIG. 3 and an RR interval summary page 250 shown in FIGS. 4-6. These pages are generated at the remote computer 116 based on the packages of data and they are selectively displayed via the UI 122. The report build page 200 facilitates analysis of cardiac events, and the RR interval summary page 250 facilitates review of RR intervals initially determined by the machine learning model 108.

FIG. 3 shows a screenshot of the report build page 200, which is used by a user to review and analyze a patient's ECG data and metadata. The report build page 200 includes multiple windows for displaying data, plots, icons, links, markers, indicators, and the like.

Window 202 displays a heart rate plot of multiple days' worth of ECG data. This window 202 provides an initial visual insight into which periods of time appear to contain abnormal heart rate activity. In the example of FIG. 3, the window 202 displays four days of ECG data, although shorter or longer time periods could be displayed by default or changed by the user.

Window 204 allows the user to view a shorter plot of ECG data. For example, the window 204 may display ECG data associated with a detected cardiac event along with ECG data preceding and following the detected event. This window 204 provides visual insight into the onset of a detected event and whether the detected event is perhaps an artifact, follow-on event, etc.

Window 208 shows a plot of ECG data (e.g., approximately 10 beats) that is shorter than the plots of windows 202 and 204. Window 208 displays a closer-up view of a portion of the ECG data of windows 202 and 204. The user can use window 204 to select which shorter set of ECG data is displayed in the window 208. Each of the windows 202,

204, and 208 can include markers, indicators, icons, etc., to visually note the location of detected cardiac events within the strips of ECG data.

RR Interval Summary Page

FIGS. 4-6 show different views or sections of the RR interval summary page 250. As noted above, RR intervals represent the time elapsed between two successive R-waves of QRS portions of ECG data. Further, determining the longest RR interval (or sets of longest RR intervals) can be challenging because of noise in ECG data and/or unidentified R-waves.

FIG. 4 shows an example of a strip of ECG data 252 with a beat that was not identified as a beat, resulting in an inaccurate RR interval measurement. The ECG data 252 shows five beats. However, only four beats 254A-254D were identified as a beat by the machine learning model 108, and the fifth beat 256 was not identified as a beat—which could have been a result of noise in the ECG signal (e.g., due to a suboptimal electrode connection with the patient).

Each identified beat 254A-254D is associated with a beat classification. In the example of FIG. 4, the first identified beat 254A is classified as a ventricular beat and denoted with an "V" while the remaining identified beats are classified as supraventricular beats and denoted with an "S". The unidentified beat 256 is not associated with beat classification.

The RR interval summary page 250 displays RR interval measurements for the identified beats. For example, the RR interval 258A for the first pair of identified beats, 254A and 254B, is shown as 1,500 milliseconds; the RR interval 258B between the second pair of identified beats, 254B and 254C, is shown as 5,708 milliseconds; and the RR interval 258C between the third pair of identified beats, 254C and 254D, is shown as 852 milliseconds. Because the beat 256 was not identified as a beat, the RR interval 258B of 5,708 milliseconds is inaccurate because the RR interval 258B is the sum of what should have been two separate RR intervals. As such, the RR interval 258B is longer than the true RR intervals.

As noted above, when reviewing a patient's cardiac activity, a physician may want to know what the length of the longest RR interval during a study was. However, due to missed or skipped beats like that noted above, some measured RR intervals may be inaccurate. The RR interval summary page 250 provides a tool to help identify and override inaccurate RR intervals.

FIG. 5 shows another view of the RR interval summary page 250 showing ECG strips associated with a small subset of the overall number of RR intervals determined by the machine learning model 108. The RR interval summary page 250 can initially display ECG strips in descending order beginning with the longest measured RR interval at the top.

Each ECG strip includes multiple beats as well as a visual indicator 260 representing the length of a measured RR interval. In FIG. 5, the visual indicator 260 is a bar outlined with a dashed line, although other designs can be used such as colored bars/strips that extend between a pair of identified beats. In instances, the visual indicator 260 is only used for the longest measured RR interval within each ECG strip. The visual indicator 260 helps the user see whether the ECG strips include a beat that was not identified by the machine learning model 108. In each of the examples in FIG. 5, it can be seen that the visual indicator 260 overlaps (or passes through) a beat positioned between a pair of identified beats. Because the skipped beat is not accounted for in the RR interval, each of the measured RR intervals shown in FIG.

5 is inaccurate and should not be used to indicate the length of the true longest RR interval.

The RR interval summary page 250 allows for a user to scroll through and view the initial RR intervals measured by the machine learning model 108. For example, the user can scroll through the RR intervals initially identified as being the longest until the user finds the actual longest RR interval. Using the RR interval summary page 250, the user can then select such RR interval as being the longest RR interval. As described in more detail below, the RR interval can be selected via the RR interval summary page 250 by selecting an override button 262 adjacent to the desired RR interval displayed on the RR interval summary page 250.

In addition to using the RR interval summary page 250 to identify which measured RR interval is the actual longest interval, the RR interval summary page 250 can be used to override inaccurate RR intervals. In short, once a user selects (via the UI 122 on the remote computer 116) an RR interval as being the longest RR interval, the RR intervals associated with time periods greater than the selected RR interval are overridden. This feature is described in more detail with respect to FIG. 6.

FIG. 6 shows a strip of ECG data with an RR interval that has been overridden. The strip of ECG data includes two beats, 270A and 270B, that were initially identified as beats by the machine learning model 108. These two beats, 270A and 270B, are associated with a beat classification, which is represented by an "S" for supraventricular for both beats, 270A and 270B. The strip of ECG data also includes one beat 272 positioned between the two identified beats 270A and 270B, that was not initially identified as a beat, and that is not associated with a beat classification. Because the beat 272 was not initially identified as a beat, the RR interval was measured between the first identified beat 270A and the second identified beat 270B which resulted in a measured RR interval that was longer than an actual RR interval. This incorrect RR interval was then overridden.

The RR interval was overridden by inserting an artifact event 274 into the strip of ECG data. As background, artifact events may be used by the machine learning model 108 to identify periods of noise or otherwise potentially unreliable portions of ECG data. For identified artifact events, systems can be programmed to ignore RR intervals associated with artifact events. For example, systems can be programmed such that any beat immediately following an artifact event cannot be used for an RR interval calculation. As such, inserting an artifact event (such as the artifact event 274) into ECG data results in certain previously calculated RR intervals to be overridden or otherwise ignored.

Therefore, once a user selects (via the UI 122 on the remote computer 116) an RR interval as being the longest RR interval, the RR intervals associated with time periods greater than the selected RR interval can be overridden by inserting an artifact event between pairs of beats within such RR intervals in the ECG data. As noted above, in certain instances, each strip of ECG data and RR interval displayed on the RR interval summary page 250 includes an override button 262 adjacent to the strip of ECG data. The user initiates the overriding process by selecting the override button 262 associated with the RR interval the user selects as the true longest RR interval. Once the override button 262 is selected, the remote computer 116 (by executing the code sent from the server 106) automatically inserts artifact events into ECG data between pairs of beats associated with RR intervals longer than the selected RR interval.

Using the above-described approach, incorrect RR intervals can be efficiently identified and ignored for purposes of analyzing RR interval data such as the longest RR interval during a study. For example, instead of manually checking and correcting each incorrect RR interval, the approach described above can automate correction of RR intervals, at least for RR intervals that are longer than the RR interval selected by the user. Once RR intervals have been overridden, the system can recalculate RR interval data (e.g., summary data such as average RR interval and the like) from the study based on the remaining RR intervals.

In certain instances, the artifact events are inserted at predetermined periods of time before an identified beat. For example, the artifact events can be inserted at 300-600 milliseconds (e.g., ~400 milliseconds) before the trailing beat of respective RR intervals. In certain instances, the inserted artifact event is an artificial event that lasts 100-400 milliseconds (e.g., ~200 milliseconds). In other instances, the artifact events can be inserted anywhere between the pairs of identified beats.

To save processing and network resources and to allow these changes to occur in real-time, the calculations and changes to the RR intervals can be carried out locally on the remote computer 116—as opposed to sending large chunks of data back and forth between the server 106 and the remote computer 116. For example, the calculations can be carried out using cache memory 124 (shown in FIG. 1) and processing capabilities (e.g., one or more microprocessors) of the remote computer 116. To enable local processing and updating, the report platform 112 can send the remote computer 116 code to execute locally. This code uses (or operates on) the outputs of the machine learning model 108 such as the measured RR intervals, which reduces the computational resources needed to process the changes made by user locally at the remote computer 116. In certain embodiments, this code is executed by an internet browser operating on the remote computer 116.

Methods

Figure 7:
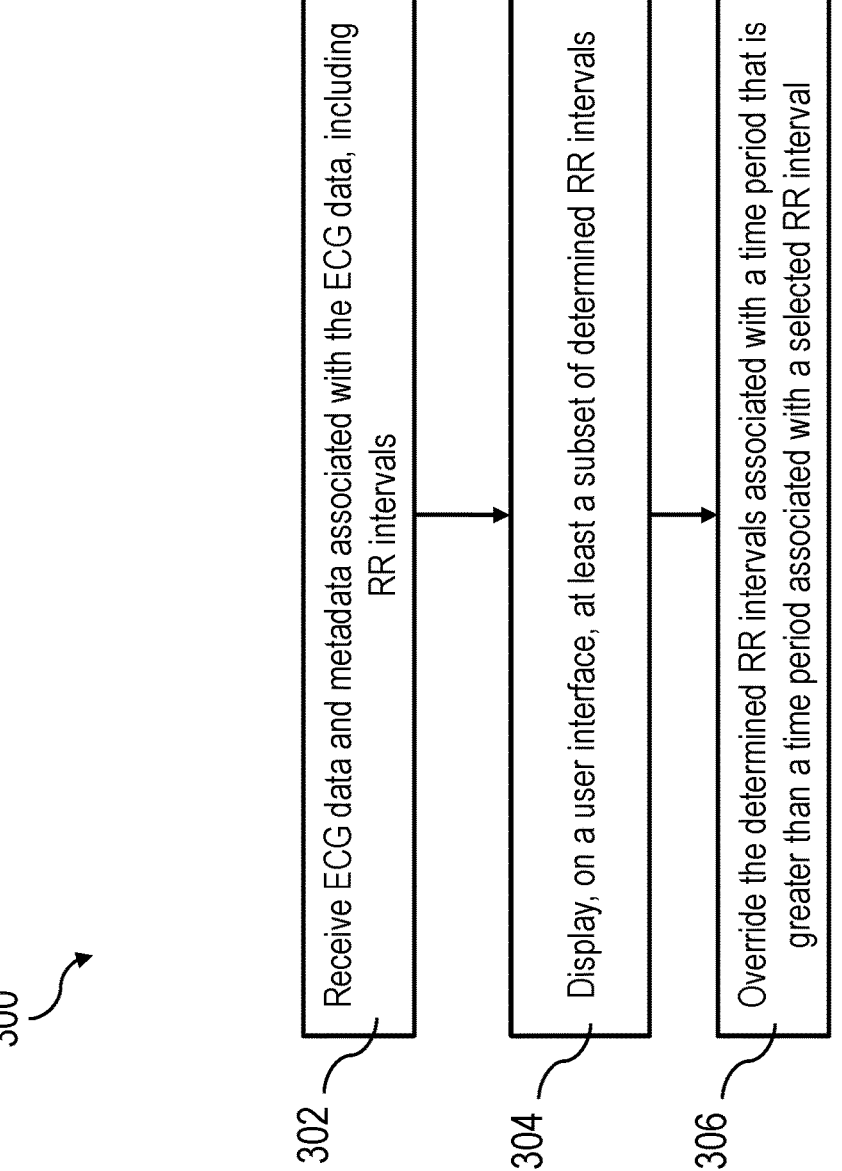
FIG. 7 shows a flow diagram depicting an illustrative method for overriding RR intervals, in accordance with instances of the disclosure.

FIG. 7 shows a block diagram of a method 300 for overriding RR intervals. The method 300 includes receiving a package of data comprising ECG data and metadata (block 302 in FIG. 7). The metadata includes determined RR intervals associated with the ECG data. The method 300 further includes displaying, on a user interface, at least a subset of determined RR intervals (block 304 in FIG. 7). The method 300 further includes overriding the determined RR intervals associated with a time period that is greater than a time period associated with a selected RR interval (block 306 in FIG. 7).

FIG. 8 shows a block diagram of a method 400 for hosting a SaaS platform and updating a hosted database in response to changes to metadata made remotely. The method 400 includes calculating, using a machine learning model operated by a server, initial RR intervals within initial ECG data (block 402 in FIG. 8). The method 400 further includes transmitting, to a remote computing system, strips of the initial ECG data and the initial RR intervals and executable code (block 404 in FIG. 8). The method 400 further includes replacing, in the database, the initial RR intervals and the initial ECG data with a new set of RR intervals calculated by the remote computing system and new ECG comprising artifact events inserted by the remote computing system (block 406 in FIG. 8).

Computing Devices and Systems

Figure 9:
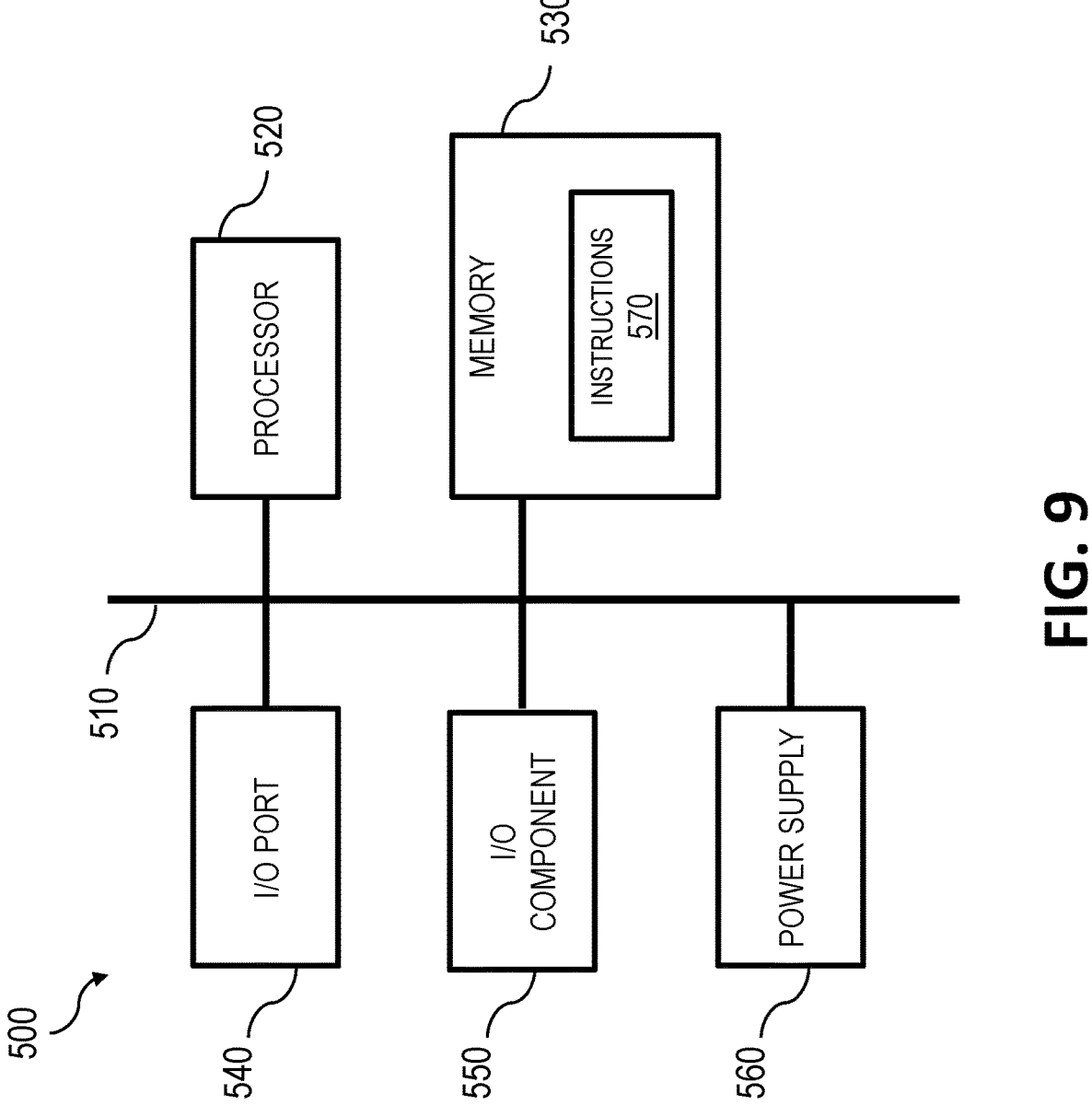
FIG. 9 shows a block diagram depicting an illustrative computing device, in accordance with instances of the disclosure.

FIG. 9 is a block diagram depicting an illustrative computing device 500, in accordance with instances of the disclosure. The computing device 500 may include any type of computing device suitable for implementing aspects of instances of the disclosed subject matter. Examples of computing devices include specialized computing devices or general-purpose computing devices such as workstations, servers, laptops, desktops, tablet computers, hand-held devices, smartphones, general-purpose graphics processing units (GPGPUs), and the like. Each of the various components shown and described in the Figures can contain their own dedicated set of computing device components shown in FIG. 5 and described below. For example, the mobile device 104, the server 106, and the remote computer 116 can each include their own set of components shown in FIG. 5 and described below.

In instances, the computing device 500 includes a bus 510 that, directly and/or indirectly, couples one or more of the following devices: a processor 520, a memory 530, an input/output (I/O) port 540, an I/O component 550, and a power supply 560. Any number of additional components, different components, and/or combinations of components may also be included in the computing device 500.

The bus 510 represents what may be one or more busses (such as, for example, an address bus, data bus, or combination thereof). Similarly, in instances, the computing device 500 may include a number of processors 520, a number of memory components 530, a number of I/O ports 540, a number of I/O components 550, and/or a number of power supplies 560. Additionally, any number of these components, or combinations thereof, may be distributed and/or duplicated across a number of computing devices.

In instances, the memory 530 includes computer-readable media in the form of volatile and/or nonvolatile memory and may be removable, nonremovable, or a combination thereof. Media examples include random access memory (RAM); read only memory (ROM); electronically erasable programmable read only memory (EEPROM); flash memory; optical or holographic media; magnetic cassettes, magnetic tape, magnetic disk storage or other magnetic storage devices; data transmissions; and/or any other medium that can be used to store information and can be accessed by a computing device. In instances, the memory 530 stores computer-executable instructions 570 for causing the processor 520 to implement aspects of instances of components discussed herein and/or to perform aspects of instances of methods and procedures discussed herein. The memory 530 can comprise a non-transitory computer readable medium storing the computer-executable instructions 570.

The computer-executable instructions 570 may include, for example, computer code, machine-useable instructions, and the like such as, for example, program components capable of being executed by one or more processors 520 (e.g., microprocessors) associated with the computing device 500. Program components may be programmed using any number of different programming environments, including various languages, development kits, frameworks, and/or the like. Some or all of the functionality contemplated herein may also, or alternatively, be implemented in hardware and/or firmware.

According to instances, for example, the instructions 570 may be configured to be executed by the processor 520 and, upon execution, to cause the processor 520 to perform certain processes. In certain instances, the processor 520, memory 530, and instructions 570 are part of a controller such as an application specific integrated circuit (ASIC), field-programmable gate array (FPGA), and/or the like. Such devices can be used to carry out the functions and steps described herein.

The I/O component 550 may include a presentation component configured to present information to a user such as, for example, a display device, a speaker, a printing device, and/or the like, and/or an input component such as, for example, a microphone, a joystick, a satellite dish, a scanner, a printer, a wireless device, a keyboard, a pen, a voice input device, a touch input device, a touch-screen device, an interactive display device, a mouse, and/or the like.

The devices and systems described herein can be communicatively coupled via a network, which may include a local area network (LAN), a wide area network (WAN), a cellular data network, via the internet using an internet service provider, and the like.

Aspects of the present disclosure are described with reference to flowchart illustrations and/or block diagrams of methods, devices, systems and computer program products. It will be understood that each block of the flowchart illustrations and/or block diagrams, and combinations of blocks in the flowchart illustrations and/or block diagrams, can be implemented by computer program instructions.

Various modifications and additions can be made to the exemplary instances discussed without departing from the scope of the disclosed subject matter. For example, while the instances described above refer to particular features, the scope of this disclosure also includes instances having different combinations of features and instances that do not include all of the described features. Accordingly, the scope of the disclosed subject matter is intended to embrace all such alternatives, modifications, and variations as fall within the scope of the claims, together with all equivalents thereof.

We claim:

1. A system comprising:
a remote computing system comprising: a user interface (UI), a first processor, and a first computer-readable medium having a first set of computer-executable instructions embodied thereon, the first set of instructions configured to be executed by the first processor to cause the first processor to:
after receiving a package of data comprising electro-cardiogram (ECG) data and metadata including determined RR intervals associated with the ECG data: display, on the UI, at least a subset of the determined RR intervals, wherein the subset comprises multiple separate strips of the ECG data;
receive, via the UI, a user selection of one RR interval from the subset, wherein the one RR interval is a selected RR interval; and
in response to the user selection, override the determined RR intervals associated with a time period that is greater than a time period associated with the selected RR interval,
wherein the override the determined RR intervals comprises inserting an artifact event between respective pairs of beats in each overridden RR interval.

2. The system of claim 1, wherein the selected RR interval is a longest true RR interval of the subset of the determined RR intervals.

3. The system of claim 1, wherein each of the RR intervals in the subset of determined RR intervals includes ECG data over multiple beats.

4. The system of claim 1, wherein each overridden determined RR interval is associated with ECG data comprising an unclassified beat.

5. The system of claim 1, wherein each overridden determined RR interval is associated with an incorrect RR interval time period.

6. The system of claim 1, wherein the artifact events are inserted at predetermined periods of time before the later-occurring of the respective pairs of beats.

7. The system of claim 1, wherein the first set of instructions are part of the package of data received from a server.

8. The system of claim 7, wherein the first set of instructions are executed by a web browser at the remote computing system.

9. The system of claim 1, further comprising:

a server comprising: a database, a second processor, and a second computer-readable medium having a second set of computer-executable instructions embodied thereon, the second set of instructions configured to be executed by the second processor to cause the second processor to:

calculate, using a machine learning model operated by the server, the determined RR intervals;

store the determined RR intervals in the database;

transmit, to the remote computing system, strips of the ECG data and the determined RR intervals and the first set of instructions;

receive a modified set of RR intervals, wherein the modified set of RR intervals include the overridden determined RR intervals; and replace, in the database, the determined RR intervals with the modified set of RR intervals.

10. A method comprising:

receiving a package of data comprising electrocardiogram (ECG) data and metadata, the metadata including determined RR intervals associated with the ECG data;

displaying, on a user interface, at least a subset of the determined RR intervals;

receiving, via the user interface, a user selection of a selected RR interval; and in response to the user selection, overriding the determined RR intervals associated with time periods that are greater than a time period associated with the selected RR interval.

11. The method of claim 10, wherein each of the overridden determined RR intervals is associated with ECG data comprising an unclassified beat.

12. The method of claim 10, wherein the overriding includes inserting an artifact event between respective pairs of beats.

13. The method of claim 12, wherein the artifact event is inserted at a predetermined period of time before the later-occurring of the respective pairs of beats.

14. The method of claim 10, further comprising:

recalculating RR interval data after the overriding the determined RR intervals.

15. The method of claim 10, wherein each RR interval is a length of time between a pair of R-waves within the ECG data.

* * * * *